United States Patent
Lobo

(10) Patent No.: US 10,806,540 B2
(45) Date of Patent: Oct. 20, 2020

(54) DEVICE AND METHOD FOR VIBRATION OF AN IMPLANTABLE DEVICE

(71) Applicant: Indiana University Research and Technology Corporation, Indianapolis, IN (US)

(72) Inventor: Brian C. Lobo, Indianapolis, IN (US)

(73) Assignee: Indiana University Research and Technology Corporation, Indianapolis, IN (US)

(*) Notice: Subject to any disclaimer, the term of this patent is extended or adjusted under 35 U.S.C. 154(b) by 593 days.

(21) Appl. No.: 15/512,467

(22) PCT Filed: Sep. 25, 2015

(86) PCT No.: PCT/US2015/052249
§ 371 (c)(1),
(2) Date: Mar. 17, 2017

(87) PCT Pub. No.: WO2016/049472
PCT Pub. Date: Mar. 31, 2016

(65) Prior Publication Data
US 2017/0296300 A1    Oct. 19, 2017

Related U.S. Application Data

(60) Provisional application No. 62/055,642, filed on Sep. 25, 2014.

(51) Int. Cl.
*A61B 90/70* (2016.01)
*A61F 2/04* (2013.01)
(Continued)

(52) U.S. Cl.
CPC .............. *A61B 90/70* (2016.02); *A61B 1/126* (2013.01); *A61F 2/04* (2013.01); *B08B 7/02* (2013.01);
(Continued)

(58) Field of Classification Search
CPC ........... A61B 1/126; A61B 90/70; A61F 2/04; B08B 7/02
See application file for complete search history.

(56) References Cited

U.S. PATENT DOCUMENTS

2005/0268921 A1    12/2005    Zumeris et al.
2006/0100548 A1    5/2006     Ferguson
(Continued)

FOREIGN PATENT DOCUMENTS

WO    WO2006124031 A1    11/2006

OTHER PUBLICATIONS

International Search Report and Written Opinion issued by the ISA/US, Commission for Patents, dated Dec. 22, 2015, for International Patent No. PCT/US2015/052249; 8 pages.

*Primary Examiner* — Sean E Conley
(74) *Attorney, Agent, or Firm* — Faegre Daniels Biddle & Reath LLP

(57) ABSTRACT

Devices for imparting vibration to implanted devices to reduce accumulation of biofilm thereon including a vibration tip, the vibration tip being sized and shaped to couple to a vibrator and receive a vibration therefrom, wherein the vibration tip is sized and shaped to conduct the vibration from the vibrator to an implanted device are disclosed. Methods of inhibiting biofilm formation including abutting a vibration source against an implanted device, and activating the vibration source to impart vibration to the implanted device thereby inhibiting a formation of biofilm on the implanted device are also disclosed.

12 Claims, 4 Drawing Sheets

(51) Int. Cl.
*B08B 7/02* (2006.01)
*B08B 17/02* (2006.01)
*A61B 1/12* (2006.01)

(52) U.S. Cl.
CPC ........ *B08B 17/02* (2013.01); *A61F 2002/044* (2013.01); *A61F 2002/046* (2013.01); *A61F 2250/0092* (2013.01)

(56) References Cited

U.S. PATENT DOCUMENTS

2008/0119845 A1  5/2008  Stone et al.
2010/0199448 A1  8/2010  Vazales et al.

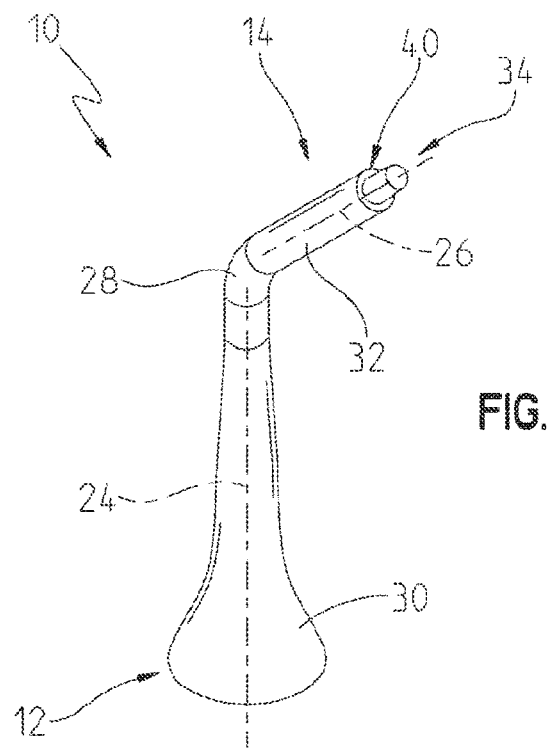
FIG. 1
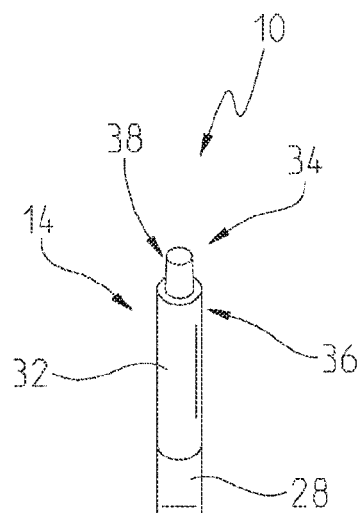
FIG. 2
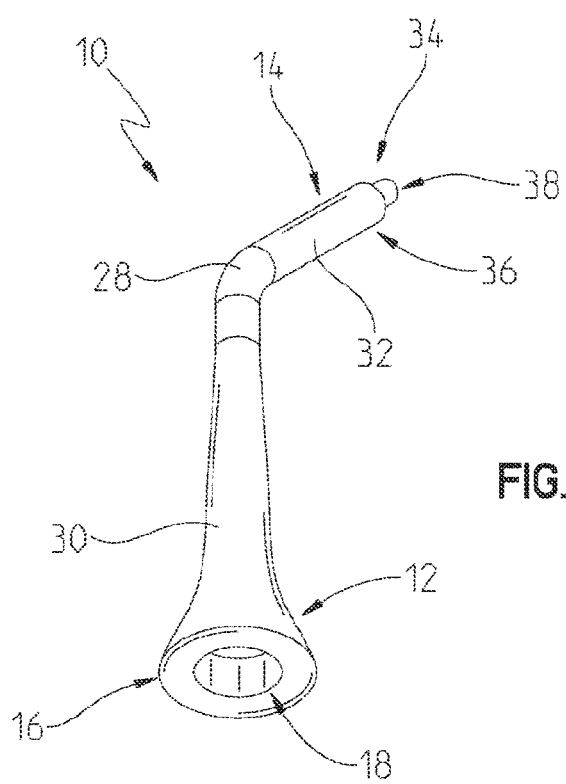
FIG. 3
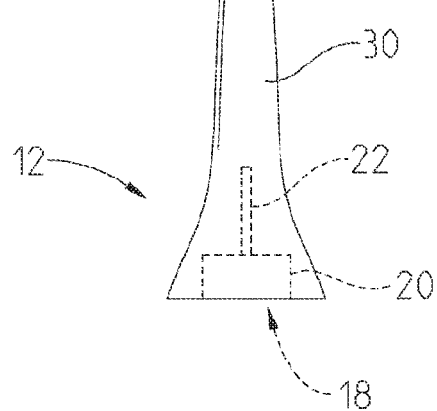

DEVICE AND METHOD FOR VIBRATION OF AN IMPLANTABLE DEVICE

CROSS-REFERENCE TO RELATED APPLICATIONS

This application is a U.S. National Stage Application of International Patent Application No. PCT/US2015/052249, filed Sep. 25, 2015, which claims the benefit of U.S. Provisional Patent Application Ser. No. 62/055,642, filed on Sep. 25, 2014, the entire disclosures of which are hereby expressly incorporated by reference in their entireties.

FIELD OF THE DISCLOSURE

The present disclosure is related to methods and devices to reduce the formation of biofilms. The disclosure is more particularly directed to methods and devices reduce the incidence of biofilm formation on implantable items by imparting vibration thereto.

BACKGROUND

Devices that are implanted in the body are subjected to the body's processes and subjected to the potential for accumulating biofilms thereon. One such device includes tracheoesophageal prostheses (TEPs). Based on their makeup, TEPs can have a device life of up to two years. However, greater than 90% of TEPs fail to adequately function to their full potential device life due to the formation of biofilm thereon. Indeed, TEPs end up needing to be switched out every 3-4 months on average. The biofilms not only coat TEPs (and other implantable devices) but infiltrate and anchor in the device (such as in the silicone of TEPs). This infiltration is able to produce leakage in a valve of the TEP, which is a failure mode thereof.

Research has been done with the aim of reducing or eliminating such biofilms from implantables. Such research has included attempts such as administering oral topical antifungals/biocidals, surface and actual material modifications (including impregnation of antibiotics), unique magnetic and multivalve designs, and dietary modifications. These attempts have been only partially successful and are often prohibitively costly and see poor compliance rates.

Accordingly, what is needed is a method and device that reduces the incidence and/or effects of biofilm formation and that does so in a way that has an ease of implementation that results in high patient compliance.

SUMMARY

Biofilm inhibitors including a vibration tip, the vibration tip being sized and shaped to couple to a vibrator and receive a vibration therefrom, wherein the vibration tip is sized and shaped to conduct the vibration from the vibrator to an implanted device are disclosed.

Also disclosed are biofilm inhibitors including a vibrator, and a vibration tip, the vibration tip being sized and shaped to couple to the vibrator and receive a vibration therefrom, the vibration tip further being sized and shaped to conduct the vibration from the vibrator to an implanted device.

Methods of inhibiting biofilm formation including abutting a vibration source against an implanted device, and activating the vibration source to impart vibration to the implanted device thereby inhibiting a formation of biofilm on the implanted device are also disclosed herein.

BRIEF DESCRIPTION OF THE DRAWINGS

The above-mentioned aspects of the present teachings and the manner of obtaining them will become more apparent and the teachings will be better understood by reference to the following description of the embodiments taken in conjunction with the accompanying drawings, wherein:

FIG. 1 is a perspective view of a first embodiment device of the present disclosure;

FIG. 2 is a side view of the device of FIG. 1 with certain internal features shown in phantom;

FIG. 3 is a bottom perspective view of the embodiment of FIG. 1;

DETAILED DESCRIPTION OF EMBODIMENTS

The embodiments disclosed herein are not intended to be exhaustive or limit the invention to the precise form disclosed in the following detailed description. Rather, the embodiments were chosen and described so that others skilled in the art may utilize their teachings.

Figure 4:
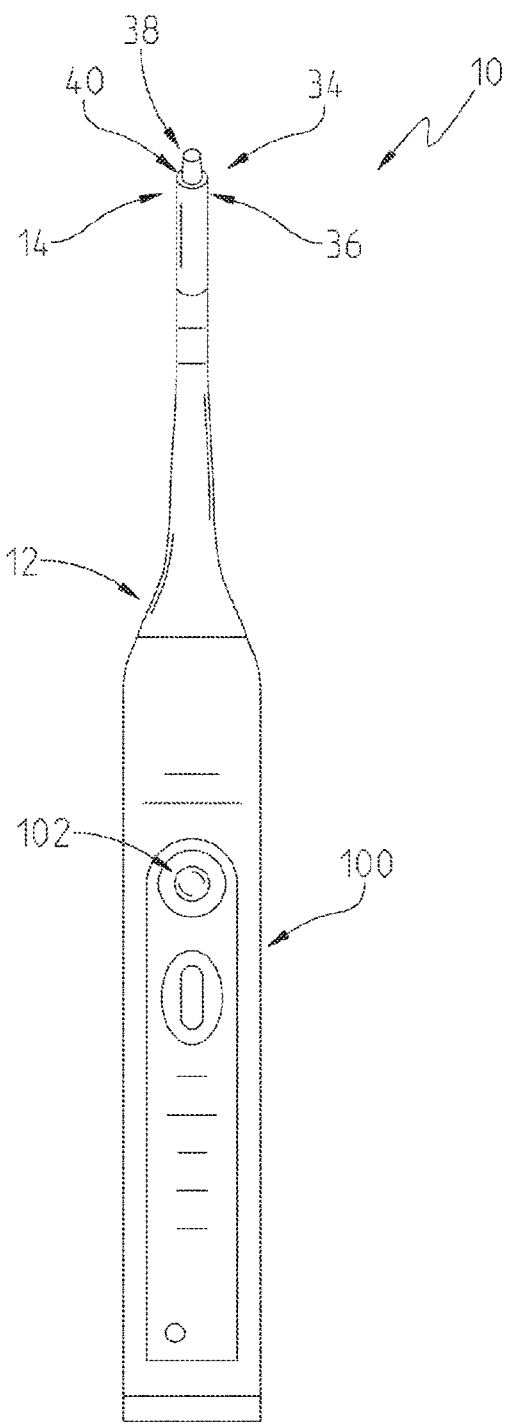
FIG. 4 is a side view of the device of FIG. 1 mounted on a base.
Figure 5:
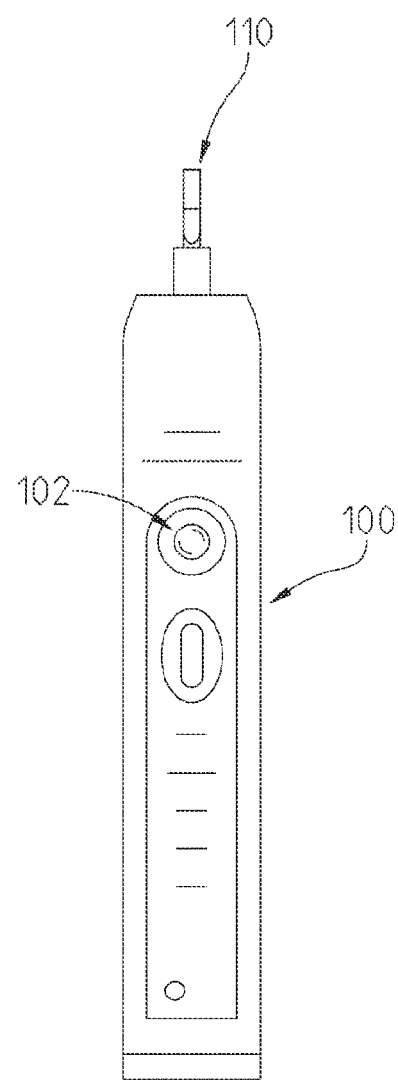
FIG. 5 is a side view of the base of FIG. 4 without the device of FIG. 1 mounted thereto.

FIG. 1 shows an exemplary vibration head 10. Vibration head 10 is illustratively formed from plastic, more specifically polypropylene. However, it should be appreciated that head 10 can be formed from any material, including plastic generally with one or more elastomers, that has sufficient stiffness to translate received vibration as described herein. Vibration head 10 includes a proximal end 12 and distal end 14. Proximal end 12 is illustratively wider than distal end 14 to match up with base 100 shown in FIG. 5. Base 100 is shown as a base produced by PHILLIPS and marketed under the name SONICARE. While the shown base 100 provides vibration as will be discussed herein, use of the specific base 100 shown in not needed. Indeed, any base 100 that is able to generate vibration and transmit that vibration to head 10 is usable within the teaching of the present disclosure. Still further, embodiments are envisioned where head 10 is integral with base 100.

Proximal end 12 of head 10 includes proximal wall 16 and mounting bore 18. Mounting bore 18 is illustratively circular. However, it should be appreciated that the shape of mounting bore 18 is chosen to mate with base 100 and thus can take on any shape needed to achieve such mounting. As shown in FIG. 2, mounting bore 18 is a multi-sectioned bore with each section having a differing diameter. First section 20 provides a friction fit on a corresponding portion of base 100. Second section 22 of mounting bore is sized to receive and abut a vibration post 110 of base 100 such that vibration of vibration post 110 is translated to head 10.

Vibration head 10 further includes an elbow portion 28. Proximal portion 30 (at proximal end 12) tapers as it extends towards elbow portion 28. Elbow portion 28 provides an angle between a proximal axis 24 of proximal portion 30 and a distal axis 26 of distal portion 32 of head 10. Elbow portion 28 illustratively provides a 120-degree angle between proximal axis 24 and distal axis 26. However, it should be appreciated that this angle is exemplary only and other angles are envisioned. The angle is generally chosen to provide desired ergonomics and ease of use during the use described herein.

Distal end 14 of head 10 includes engagement portion 34. In the shown embodiment, engagement portion 34 is sized and shaped to engage a TEP. It should be appreciated that the specific shape of engagement portion 34 is chosen based upon the specific implementation. Thus, while the shape and dimensions shown are configured to engage a TEP, other shapes and dimensions would likely be chosen when the item to which vibration is being imparted is other than a TEP. Indeed embodiments are envisioned to impart vibration to any number of devices that are exposed to biofilm-forming environments (pacemakers, cochlear implants, etc.)

The illustrated example of engagement portion includes a first diametered portion 36, a second diametered portion 38, and a shoulder 40 at a common boundary for first diametered portion 36 and second diametered portion 38. Second diametered portion 38 is distal of first diametered portion 36 and provides the distal-most portion of head 10. Second diametered portion 38 has a diameter that is smaller than a diameter of the first diametered portion 36. The diameter of the second diametered portion 38, in the present case, is chosen to fit within a bore in a TEP. The diameter of the first diametered portion 36, in the present case, is chosen so that it is too large to fit within the bore of the TEP. The length of the second diametered portion 38 is chosen such that shoulder 40 engages the TEP to arrest further advancement of head 10 into the TEP before the second diametered portion 38 is able to extend an undesired amount. In one embodiment, the second diametered portion 38 has a length equal to the depth of the bore in the TEP engaged by the head such that the second diametered portion 38 is unable to extend into the body beyond the TEP. Embodiments are envisioned having other lengths of second diametered portion 38. The diameter of the second diametered portion 38 is illustratively chosen to snugly fit within the bore of the TEP. Embodiments are envisioned where second diametered portion 38 is externally textured, grooved, and/or includes bristles.

In operation, as mentioned above, a user positions distal end of head (the second diametered portion 38) within the bore of the TEP and advances the second diametered portion 38 until shoulder 40 abuts the TEP. Button 102 on base 100 is then pressed to activate base 100. This activation causes vibration post 110 to vibrate. This vibration is transmitted to head 10. Vibration of head 10 is transmitted to the abutting TEP.

Figure 6:
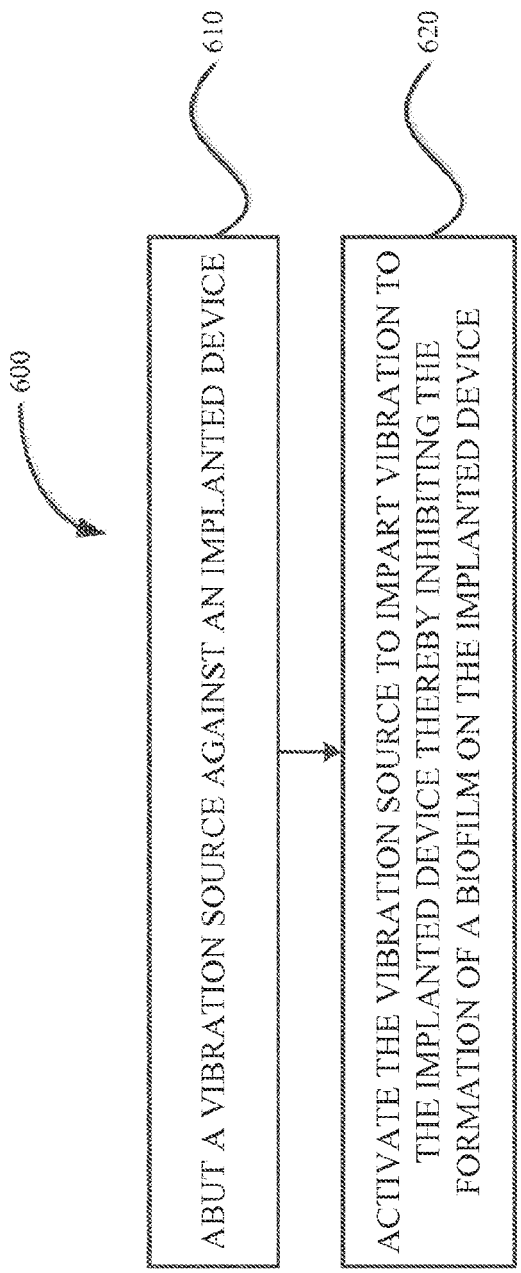
FIG. 6 illustrates a method of inhibiting biofilm formation according to various embodiments.

For example, with reference to FIG. 6, method 600 of inhibiting biofilm formation is illustrated. Method 600 comprises abutting a vibration source against an implanted device (step 610), such as a medical device (e.g., tracheoesophageal prostheses) and then activating the vibration source to impart vibration to the implanted device (step 620). Thus, various systems and methods may cause an implanted device (e.g., an implanted medical device) to vibrate. In various embodiments, the vibration of the device slows, eliminates, and/or at least partially reverses biofilm growth and/or infiltration into the device, such as a TEP. Accordingly, regular vibration of the TEP is expected to prolong the useful life of the TEP.

Comparative Data

Overview

Ex vivo tracheoesophageal prostheses were obtained and prostheses demonstrating physical integrity and an absence of gross biofilm accumulation were utilized. 16 prostheses were cleansed and sterilized prior to random placement by size in two modified Robbins devices arranged in parallel. Each device was seeded with a polymicrobial oral flora on day 1 and received basal artificial salivary flow continuously with three growth medium meals daily. One device was randomly selected for vibratory stimulus and 2 minutes of vibration was applied to each prosthesis before and after meals for 5 days. The prostheses were explanted, sonicated, and the biofilm cultured for enumeration. This process was repeated after study arm crossover.

Tracheoesophageal prostheses in the dynamic model receiving vibratory stimulus demonstrated reduced gross biofilm accumulation and a significant biofilm colony forming unit per milliliter reduction of 5.56-fold compared to non-vibratory controls ($p<0.001$). Significant reductions were observed within size subgroups.

It was found, as explained in further detail below, that application of vibratory stimulus around meal times significantly reduces biofilm accumulation on tracheoesophageal prostheses in a dynamic in vitro model.

In this experimental comparison, a polymicrobial suspension of oral flora including *Candida albicans, Candida tropicalis, Streptococcus salivarius, Rothia dentocariosa, Staphylococcus aureus*, and *Staphylococcus epidermidis* was applied to TEPs partially submerged in growth medium in sterile well culture plates. Vibratory stimulus was applied to the treatment group during a 4 day growth course. Cultures that were made from TEPs after completion of the growth course demonstrated some reduction in colony forming unit (CFU) per milliliter (mL) in those treated with the vibratory stimulus compared to controls.

Experimental Methods

Tracheoesophageal Voice Prostheses Preparation

Expired and ex vivo Atos Medical® (available from West Allis, Wis.) Provox® 2 low-resistance, indwelling silicone voice prostheses of 22.5 French (F) internal diameter and shaft length sizes 6 millimeter (mm), 8 mm, and 10 mm were utilized for this experiment. The included TEPs were individually scrubbed, sonicated for 15 seconds (s), rinsed with deionized water, disinfected for 30 minutes (min) in 70% ethanol, and dried in aseptic conditions prior to loading into the Robbins devices. TEPs were arranged by size and then equal quantities of the sized groups were randomly assigned to placement in either the vibration arm Robbins device or the control arm Robbins device.

Robbins Device Setup

Robbins devices are common systems used in microbiological studies on biofilm formation. The basic experimental setup involves a closed system of tubing with an influent source of liquid nutrition moved by a peristaltic pump through a unidirectional device chamber which has effluent tubing to waste. A Robbins device that emulated the tracheoesophageal puncture site interface was used for this experimental comparison.

The experimental setup involved three separate influent sources containing 1) normal saline (representing saliva), 2) a 1:1 mixture growth medium (GM) of Brain Heart Infusion (BHI) and Yeast Extract-Peptone-Dextrose (YPD) broths, and 3) a smaller 1:1 mixture GM of BHI and YPD broths to be inoculated (after autoclaving) with a polymicrobial culture of *C. albicans, C. tropicalis, S. salivarius, R. dentocar-*

*iosa, S. aureus,* and *S. epidermidis*. Preliminary testing demonstrated that a 1:1 mixture GM of BHI and YPD broths was appropriate for growth of polymicrobial biofilms on TEPs and that appreciable biofilm accumulation could be observed over the course of 4 to 5 days. Autoclavable tubing from the three fluid sources were Y-connected together before splitting into separate parallel tubing through 2 cassettes in an Ismatec® Reglo Digital 2 channel peristaltic pump (available from IDEX Corp, Wertheim, Germany). From the pump, the parallel tubing connected to the influent spigots of two Robbins devices each with effluent spigot tubing dumping into an effluent beaker. The parallel Robbins devices were utilized in an effort to create a microcosmic dynamic tracheoesophageal puncture site interface while reducing intergroup variability as each Robbins device received the same influent fluids and flow rates from the same source containers. The entire system of flasks, tubing, and Robbins devices was autoclaved to ensure internal sterility prior to starting the experimental run in an aerobic 5% $CO_2$ incubator set at 37° C.

Inoculation, Simulated "Meal" Feeding Cycles, and Biofilm Formation

Twelve hours prior to placement of the experimental system in the aerobic incubator, individual broth cultures of *C. albicans, C. tropicalis, S. salivarius, R. dentocariosa, S. aureus,* and *S. epidermidis* were inoculated and incubated aerobically with 5% $CO_2$ at 37° C. On the first morning of the experiment, 1 mL of each of these culture broths were aseptically added to the smaller GM container to provide polymicrobial inoculation of the Robbins devices. During the first day of the experimental run, the inoculated GM was pumped through the system at a rate of 1 mL/min for 30 min on 3 occasions to simulate 3 meals evenly spaced throughout the day. A normal saline flow rate of 0.5 mL/min between meals simulates wakeful unstimulated salivary flow rates whereas a rate of 0.1 mL/min simulates resting salivary flow rates between evening and morning. On experimental days 2 through 5, the sterile GM source was utilized to simulate meals as the system was adequately inoculated. The entire experimental setup was maintained in the aerobic incubator at 37° C. while biofilm formed over 5 days.

Mechanical Vibration Application

One Robbins device was randomly selected to have its TEPs undergo mechanical vibration. Vibration was applied to TEPs mounted in the treatment group Robbins device by a motor oscillating at approximately 260 Hz for 2 min duration before and after each "meal" to simulate when vibration would reasonably be performed by a patient. This vibration frequency and duration has proven safe for long term intraoral use for prevention of dental caries by electric toothbrush manufacturers.

Biofilm Culturing and Colony Counting

At the conclusion of 5 days, the TEPs were aseptically removed individually from the Robbins devices, unbound bacteria were gently rinsed away with sterile normal saline, and the TEPs were placed in individual 50 mL sterile conical centrifugation tubes containing 5 mL of sterile saline. Each explanted TEP was then vortexed for 15s, sonicated for 15s, and again vortexed for 15 s to release the biofilm microorganisms into suspension. For each TEP, the 5 mL undiluted biofilm suspensions were diluted 1:200 and 1:1,000 prior to duplicate culturing of each dilution onto 2 blood agar plates with a spiral plating apparatus. The culture plates were left to dry at room temperature for 15 min prior to aerobic incubation with 5% $CO_2$ for 36 hours. The ProtoCOL® 1 automated colony counting system (SYNBIOSIS, Frederick, Md.) was utilized to determine CFU/mL for each plate. Three measurements each for the 2 blood agar plates for the 1:1,000 dilution were averaged as they demonstrated appropriately countable colony density. The 1:200 plates were not counted because of the high density of the colonies.

Experimental Crossover and Duplication

At the conclusion of the 5 day experimental run and after counting the biofilm colonies, the entire Robbins device system (including the TEPs) was disassembled and decontaminated with 70% ethanol prior to scrubbing, rinsing with deionized water, and reassembly. New GM and normal saline were prepared and the TEPs were replaced in fresh silicon sheets within the Robbins device chambers. The experimental system was again run with the previously described inoculation methods, flow rates, and time frames. However, during the duplication run the TEPs underwent experimental arm crossover and the previously non-vibration group had mechanical vibration applied as described above. Subsequently, the TEPs underwent explantation, culturing, and colony counting with the same methods as the first run.

Statistical Considerations

The coefficient of variation in this comparative experiment was anticipated to be approximately 0.6 based on a prior study. Therefore, with a total sample size of 12 per group, the comparison was anticipated to have 80% power to detect a 2 times difference in CFU/mL between groups, at an alpha of 5% significance level. Because of the plan for subgroup analysis by size, a total of 16 TEPs were utilized in each run (8 per Robbins device). Each Robbins device was populated by four 6 mm length TEPs, three 8 mm TEPs, and a single 10 mm TEP. Grouping of TEPs into the treatment Robbins device or control Robbins device was randomized by size. A paired-samples t-test was utilized for cumulative treatment arm analysis and to compare vibratory versus non-vibratory groups at different TEP sizes. Insufficient blood agar resulted in an inability to culture and measure biofilm formation in the non-vibratory group's TEP size 10 sample. Consequently, the paired vibratory size 10 sample was excluded from paired analysis. An independent-samples two-tailed t-test was used for intra-run analysis between vibratory and non-vibratory groups and for inter-run analysis (vibratory versus vibratory; non-vibratory versus non-vibratory). A one-way ANOVA was used to compare the effect of TEP size on CFU/mL cultured. A natural log (ln) transformation was performed to allow for parametric analysis. All variance within paired analysis was expressed as standard error of the mean (SEM) of the differences between paired samples. The variance within one-way ANOVA and independent-samples t-tests was expressed as SEM. Statistical analysis was accomplished using SPSS® 22 (available from IBM Corp).

Experimental Results

Figure 7:
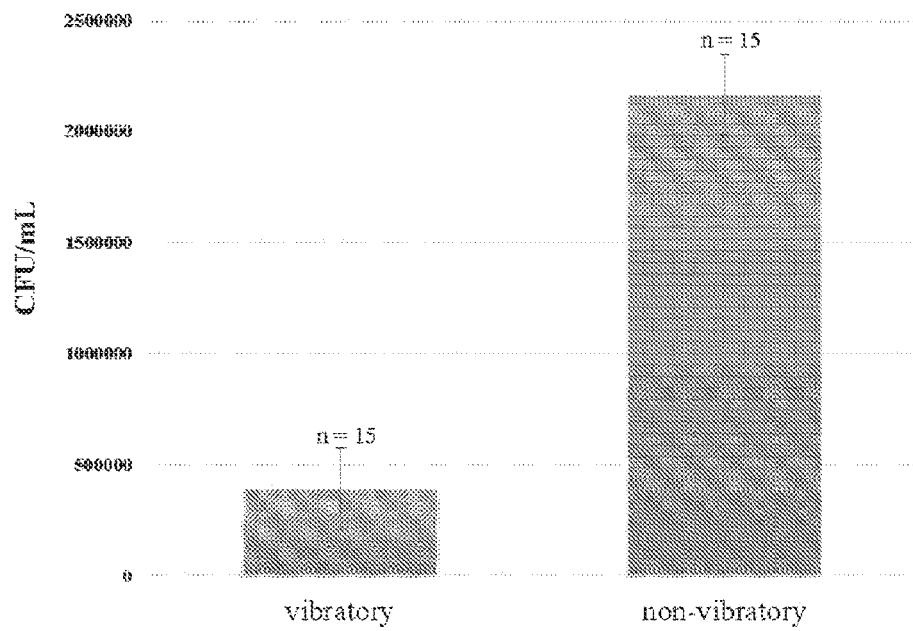
FIG. 7 illustrates a comparison of paired vibratory and non-vibratory groups with various tracheoesophageal prostheses (TEPs) sizes.

When comparing all vibratory TEPs to non-vibratory TEPs for both experimental runs, there was a statistically significant 5.56-fold reduction in mean CFU/mL, as shown in FIG. 7 and Table 1 below. As illustrated in FIG. 7 and Table 1 (below), the vibratory group's mean CFU/mL ($0.39 \times 10^6 \pm 0.072 \times 10^6$) is significantly different than the non-vibratory group ($2.2 \times 10^6 \pm 0.41 \times 10^6$); t (14), p=0.00025. The error bars in FIG. 7 represent SEM of the differences between paired samples.

an overall statistically significant 5.56-fold reduction in biofilm accumulation. Moreover, the statistically significant reduction in CFU/mL was observed in TEP size 6 and 8 subgroup analyses as well (as shown in Table 1 above). As TEP size increased, the proportional reduction in CFU/mL also increased; a 5.0 fold reduction for size 6 mm TEPs and

TABLE 1

Comparison of mean CFU/mL formed in vibratory and non-vibratory groups based on TEP size

| TEP size | Vibratory group (CFU/mL) | Non-vibratory group (CFU/mL) | (n) | t-value | Sig. |
|---|---|---|---|---|---|
| 6 | $0.30 \times 10^6 \pm 0.11 \times 10^6$ | $1.5 \times 10^6 \pm 0.11 \times 10^6$ | 16 | t(7) = −5.64 | 0.00078* |
| 8 | $0.44 \times 10^6 \pm 0.33 \times 10^6$ | $2.5 \times 10^6 \pm 0.33 \times 10^6$ | 12 | t(5) = −3.10$^a$ | 0.027*$^a$ |
| 10 | $0.79 \times 10^6$ (n = 1) | $5.7 \times 10^6$ (n = 1) | 2 | | |
| Combined | $0.39 \times 10^6 \pm 0.18 \times 10^6$ | $2.2 \times 10^6 \pm 0.18 \times 10^6$ | 30 | t(14) = −4.86 | 0.00025* |

Note.
The combined group represents cumulative data including all TEP sizes
Note.
TEP = tracheoesophageal voice prosthesis;
CFU = colony forming unit
Note.
P-values (Sig.) are derived from paired samples t-tests comparing vibratory and non-vibratory groups within each row.
SEM of the differences between paired samples is used to express variability.
$^a$Statistical analysis could not be performed due to insufficient sample size in TEP size 10 group
*Denotes statistical significance at 95% confidence interval (p < 0.05)

When comparing the treatment arm to the control arm for each run individually, significant reductions in CFU/mL were also observed. The first run showed a statistically significant 3.6-fold reduction between the mean CFU/mL ($2.0 \times 10^6 \pm 0.21 \times 10^6$ CFU/mL (non-vibratory group) versus $0.55 \times 10^6 \pm 0.10 \times 10^6$ CFU/mL (vibratory group); t(13)=−6.39, p=0.000024). Within the second run there was a significant 9.4-fold reduction between the non-vibratory and vibratory mean CFU/mL with analysis following a natural log transformation: $14.4 \pm 0.28$ ln(CFU/mL) versus $12.2 \pm 0.25$ ln(CFU/mL); (t(14)=5.70, p=0.000055).

Since there was a wide range in reduction of biofilm between the first and second runs (3.6-fold versus 9.4-fold, respectively), post-hoc subgroup analyses were performed. The first run's non-vibratory group mean CFU/mL was compared to the second run's non-vibratory group, and no significant difference was observed following a natural log transformation ($14.4 \pm 0.12$ ln(CFU/mL) versus $14.4 \pm 0.28$ ln(CFU/mL); t(13)=0.26, p=0.80). The vibratory group mean CFU/mL between the first and second runs were similarly analyzed, and in this case a significant difference was observed ($0.55 \times 10^6 \pm 0.010 \times 10^6$ CFU/mL versus $0.25 \times 10^6 \pm 0.062 \times 10^6$ CFU/mL; t(14)=2.60, p=0.021).

Figure 8:
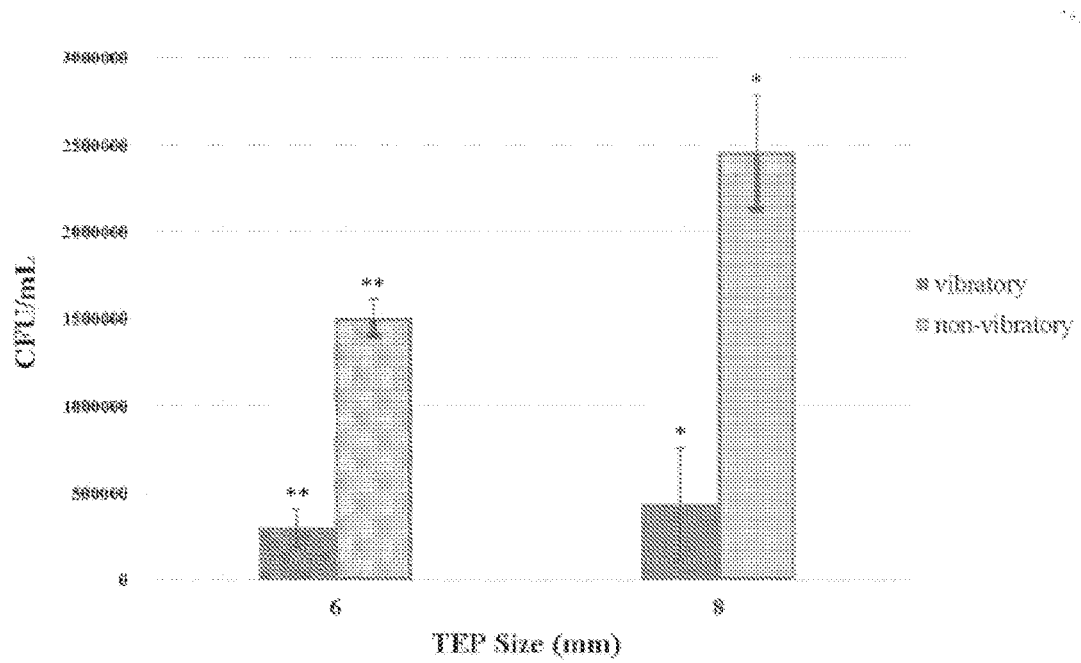
FIG. 8 illustrates a comparison of the TEP sizes for samples with vibratory and non-vibratory groups.

For all TEP size subgroups analyzed, significant reductions in mean CFU/mL were observed after vibratory treatment with a trend toward higher CFU/mL reduction in larger TEP sizes as illustrated in Table 1 and FIG. 8. As illustrated in FIG. 8, there were statistically significant differences between vibratory and non-vibratory groups with TEP sizes 6 and 8, where *=p<0.05; **=p<0.001 comparing vibratory and non-vibratory groups at each TEP size. Error bars represent SEM of the differences between paired samples.

One-way ANOVA comparing mean CFU/mL demonstrated no significant difference between sizes 6 mm, 8 mm, or 10 mm groups in both the vibratory treatment group (F2,13=1.55, p=0.25) and non-vibratory group (F2,12=3.84, p=0.052).

The experimental results of the in vitro model of the tracheoesophageal puncture site interface demonstrated that the application of mechanical vibration to TEPs resulted in a 5.6 fold reduction for size 8 mm TEPs. This may be related to the potential stasis of growth medium and bacteria within the longer TEP shaft by capillary forces. Prolonged stasis of sonicated biofilm elements may allow more rapid re-accumulation of biofilm in these larger TEPs. Analysis revealed that within both the vibratory and non-vibratory groups, size did not significantly affect CFU/mL cultured. Therefore, mechanical vibration appears to have the strongest effect among the potential variables influencing biofilm formation in this study.

Moreover, the parallel arrangement of Robbins devices within a run and the crossover of treatment arms between runs confirmed that the reduction in CFU/mL was not likely related to local growing condition variability nor intrinsic susceptibility for biofilm formation by a subset of TEPs included in the study. Despite endeavoring to reduce variability, it should be noted that between the first and second run, there existed a significant difference in CFU/mL between each run's vibratory group while finding no difference between each run's non-vibratory group. One explanation for this is found in the intrinsically stochastic nature of polymicrobial cultures. There is a possibility that different bacterial species' success was variable in early TEP adherence, and that some of these species are more resistant to the biofilm reducing effect of vibration. All culture plates demonstrated polymorphic colony types consistent with polymicrobial growth, but speciation techniques were not utilized. Despite the difference between the two runs' vibratory groups, however, each vibratory group was significantly different compared to its non-vibratory counterpart within their respective runs.

The above detailed description and the examples described therein have been presented for the purposes of illustration and description only and not for limitation. For example, the operations described may be done in any suitable manner. The method may be done in any suitable order still providing the described operation and results. It is therefore contemplated that the present embodiments cover any and all modifications, variations or equivalents that fall within the spirit and scope of the basic underlying principles disclosed above and claimed herein.

What is claimed is:

1. A method of inhibiting biofilm formation on an implanted tracheoesophageal prostheses including a bore having a diameter, including:
   abutting a vibration tip of a vibration source in the bore of the implanted tracheoesophageal prostheses, wherein:
   the vibration tip comprises an engagement portion configured to engage with the implanted tracheoesophageal prostheses;
   the engagement portion comprises a first diametered portion and a second diametered portion distal of the first diametered portion;
   the second diametered portion has a diameter that is smaller than the first diametered portion and configured to fit within the bore of the tracheoesophageal prostheses; and
   the first diametered portion is configured to not fit within the bore of the of the tracheoesophageal prostheses; and
   activating the vibration source to impart vibration to the implanted tracheoesophageal prostheses by the vibration tip thereby inhibiting a formation of biofilm on the implanted tracheoesophageal prostheses.

2. The method of claim 1 wherein the vibration tip is formed from a plastic.

3. The method of claim 2, wherein the plastic comprises polypropylene.

4. The method of claim 1 wherein the vibration tip comprises a mounting bore.

5. The method of claim 4, wherein the mounting bore is circular.

6. The method of claim 4, wherein the mounting bore is multi-sectioned.

7. The method of claim 6, wherein the multi-sectioned mounting bore comprises a plurality of sections having different diameters.

8. The method of claim 1 wherein the vibration tip comprises an elbow portion proximal to the engagement portion.

9. The method of claim 8, wherein the elbow portion provides a 120-degree angle between a proximal axis and a distal axis of the vibration tip.

10. The method of claim 1 wherein the vibration tip comprises a proximal end that is wider than a distal end.

11. The method of claim 1 wherein the second diametered portion has a length equal to a depth of the bore in the tracheoesophageal prostheses.

12. The method of claim 1 wherein:
    the vibration tip is sized and shaped to couple to the vibration source and receive a vibration therefrom; and
    the method further including the vibration source.

* * * * *